US009295593B2

(12) United States Patent
Van Malderen

(10) Patent No.: US 9,295,593 B2
(45) Date of Patent: Mar. 29, 2016

(54) ENVIRONMENTALLY FRIENDLY ABSORBENT STRUCTURE

(75) Inventor: Bart Van Malderen, Hamme (BE)

(73) Assignee: VYNKA BVBA, Hamme (BE)

( * ) Notice: Subject to any disclaimer, the term of this patent is extended or adjusted under 35 U.S.C. 154(b) by 145 days.

(21) Appl. No.: 13/880,443

(22) PCT Filed: Oct. 20, 2011

(86) PCT No.: PCT/EP2011/005285
§ 371 (c)(1),
(2), (4) Date: Jul. 3, 2013

(87) PCT Pub. No.: WO2012/052172
PCT Pub. Date: Apr. 26, 2012

(65) Prior Publication Data
US 2015/0038929 A1  Feb. 5, 2015

(30) Foreign Application Priority Data

Oct. 20, 2010  (EP) .................................. 10447026

(51) Int. Cl.
*A61F 13/15*  (2006.01)
*A61F 13/532*  (2006.01)
(Continued)

(52) U.S. Cl.
CPC ....... *A61F 13/5323* (2013.01); *A61F 13/15203* (2013.01); *A61F 13/15699* (2013.01);
(Continued)

(58) Field of Classification Search
CPC .............. A61F 13/5323; A61F 13/515; A61F 13/15203; A61F 13/53; A61F 2013/51026; A61F 2013/530481; A61F 2013/530562; A61F 2013/53051

USPC .......... 604/378, 385.101, 379, 380, 365, 368, 604/374, 375, 367
See application file for complete search history.

(56) References Cited

U.S. PATENT DOCUMENTS 4,381,783 A  5/1983  Elias

FOREIGN PATENT DOCUMENTS

EP  0146190  * 12/1984  .............. A61F 13/18
EP  1447066 A1  8/2004
(Continued)

OTHER PUBLICATIONS

International Search Report for PCT/EP2011/005285, mailed Feb. 8, 2012; ISA/EP.

*Primary Examiner* — Jacqueline Stephens
(74) *Attorney, Agent, or Firm* — Harness, Dickey & Pierce, P.L.C.

(57) ABSTRACT

The present invention relates to an absorbent structure, preferably for use in absorbent articles as used in the personal hygiene industry such as feminine hygiene garments, baby diapers and pants or adult incontinence garments. The present invention also relates to an absorbent article comprising such absorbent structure and to a method of manufacturing the absorbent structure. The absorbent structures comprise a carrier layer, an auxiliary layer and an absorbent material there between wherein substantially permanent primary attachments and substantially temporary secondary attachments join the carrier layer and auxiliary layer at least partially together, whereby the substantially temporary secondary attachments are loosened as a result of exposing the absorbent structure to a liquid whereas the substantially permanent primary attachments remain substantially intact. The present invention foresees in the need for improved flexible, thin, lightweight absorbent structures for an absorbent article which overcomes the absorbency problems of the prior art during absorption, distribution and retention of liquids with optimal fit.

17 Claims, 7 Drawing Sheets

(51) Int. Cl.
*A61F 13/539* (2006.01)
*A61F 13/515* (2006.01)
*A61F 13/53* (2006.01)
*A61F 13/51* (2006.01)

(52) U.S. Cl.
CPC ............ *A61F13/515* (2013.01); *A61F 13/539* (2013.01); *A61F 2013/51026* (2013.01); *A61F 2013/530481* (2013.01); *A61F 2013/530562* (2013.01); *A61F 2013/530868* (2013.01)

(56) References Cited

FOREIGN PATENT DOCUMENTS

| | | |
|---|---|---|
| EP | 1 632 206 A1 | 3/2006 |
| GB | 2 283 680 A | 5/1995 |
| WO | WO-95/11654 A1 | 5/1995 |
| WO | WO-95/17868 A1 | 7/1995 |
| WO | WO-95/21596 A1 | 8/1995 |

\* cited by examiner

ENVIRONMENTALLY FRIENDLY ABSORBENT STRUCTURE

CROSS-REFERENCE TO RELATED APPLICATIONS

This application is a 371 U.S. National Stage of International Application No. PCT/EP2011/005285, filed on Oct. 20, 2011, which claims priority to European Patent Application No. 10447026.5, filed Oct. 20, 2010, the contents of which are hereby incorporated by reference in their entirety as if fully set forth herein.

FIELD OF THE INVENTION

The present invention relates to an environmentally friendly absorbent structure, preferably for use in absorbent products, such as for example absorbent articles as used in the personal hygiene industry (e.g. feminine hygiene garments, baby diapers and pants, adult incontinence garments). The present invention also relates to an absorbent article comprising such absorbent structure and to a method of manufacturing said absorbent structures.

BACKGROUND OF THE INVENTION

There has been increasing demand in recent years for flexible, thinner, lightweight absorbent structures to resolve various problems of manufacturing, marketing, design, fit, wearing comfort, distribution, garbage disposal, material and energy consumption, transportation and storage costs and the like.

It is known from the art to introduce absorbent particulate polymer material into a matrix of cellulose fibers so as to create an absorbent structure whereby the absorbent particulate polymer material is capable of absorbing, distributing and retaining liquid while the cellulose fiber matrix acts as a grid, keeping absorbent particulate polymer material in its desired location. However, since the presence of cellulose fibers, usually wood pulp or fluff, results in relatively thick and bulky products, the process of manufacturing fluff involves cutting down trees and treating the wood pulp with various chemicals and transportation of the raw materials and end product is typically done over relative large distances, the product and process is considered to be less environmentally friendly. Hence there has been a desire to manufacture such absorbent structures without the use of wood pulp.

Many attempts have been undertaken to manufacture flexible, thin and lightweight absorbent structures, consisting of an absorbent material bonded to one or more carrier layers. However, the physical and/or chemical interaction in between the absorbent material and the bonding material and/or the carrier material often leads to a reduced absorption, distribution and/or retention performance despite functional and/or structural requirements.

It has been found that it is important to at least partially immobilise the absorbent material by compartmentalizing, restraining and/or bonding it to the absorbent structure in such a way that the absorbent structure is able to hold the absorbent material in either dry, partially or fully liquid loaded state. Failing to provide said sufficient structural integrity results in loss of functional performance such as absorbent structure coherence, absorption and/or retention performance and partial or overall failure.

Moreover, it is equally important not to excessively restrict the absorbent material from expanding and/or swelling during the liquid uptake, as this would also have a negative impact on the absorption and/or retention performance of the absorbent structure.

Many efforts have tried to compromise in between securely immobilizing absorbent material within the absorbent structure, while still sufficiently allowing the absorbent material to freely expand and swell during use, which in relation to absorbent articles within the personal hygiene industry for instance include:

U.S. Pat. No. 4,381,783 discloses an absorbent article with an absorbent structure comprising pockets of absorbent polymer material. These pockets are provided as to confine the movement of the absorbent polymer material, in particular when the absorbent article is partially or fully loaded with bodily exudates. These pockets form part of an absorbent storage layer and are typically provided from cellulose fibres. Hence, as to achieve good immobilization of the absorbent polymer material according to the teaching of this patent relatively high amounts of cellulose fibre material are required, thus increasing cost, bulkiness and rigidity of the absorbent article and severely reducing and hindering the expansion and/or swelling capacity of the absorbent polymer materials. The provision of such pockets may also hinder the free distribution of liquids to the more absorbent areas of the absorbent core, for example the areas of absorbent polymer materials.

WO95/17868 discloses an absorbent structure comprising two fibre layers and an intermediate layer. This intermediate layer comprises an absorbent polymer material in an amount exceeding 120 g/m² and particles of a thermoplastic material. While this construction certainly provides good immobilisation of the absorbent polymer material in the dry state, it seems that only a lesser immobilisation can be achieved in the liquid loaded state. The thermoplastic material appears to stretch to a much lesser extent than the potential swelling of the absorbent polymer materials. Therefore, in particular when the absorbent structure is to be used in an absorbent article to absorb and retain high amounts of bodily exudates, for example a diaper or pants, the absorbent structure disclosed herein may not be fully satisfactory.

EP724418 discloses an absorbent article which includes absorbent polymer material located in discrete pockets. The absorbent article comprises a first and a second carrier layer and water-sensitive attaching means for securing together the carrier layers and to provide a plurality of pocket regions. The article comprises absorbent polymer material located within said pocket regions. The water-sensitive attachment means provides a wet strength which is less than the separating force imparted by a swelling of that absorbent polymer material when that absorbent polymer material is exposed to bodily exudates. The absorbent article is said to provide an absorbent structure which more securely locates and contains the absorbent polymer material in a selected way of pockets when the article is dry. However, due to the construction of the pockets, and specifically due to the selection of the water-sensitive attachment means, these pockets are not able to be controlled when the article is partially or fully loaded with liquids. Therefore, it is believed that this absorbent article does not provide a satisfactory immobilization of the absorbent material in partially or fully liquid loaded state leading to functional/structural failure.

EP1447066 describes an absorbent core for an absorbent article which provides an improved immobilization of absorbent polymer material when the article is fully or partially bodily exudates loaded. Specifically disclosed is an absorbent core useful in an absorbent article comprising a non-woven substrate layer, a layer of thermoplastic material in the form of a hot melt adhesive which bonds to the substrate layer to define cavities there between, and an absorbent material held in these cavities. However, in order to adequately secure the absorbent material, one needs to use a significant amount of thermoplastic material, which leads to higher costs and more product rigidity. Also, due to its internal cohesion, the layer of thermoplastic material exerts pressure and offers resistance against the free swelling of the absorbent material. Furthermore the high quantities of thermoplastic material may often lead to shielding and/or blocking of the absorbent polymer materials leading to reduced absorption and retention performance. Therefore, it is believed that this absorbent core does not provide satisfactory immobilization of absorbent materials in liquid loaded states. Additionally, the use of thermoplastic materials, glue or adhesives is considered to be less environmentally-friendly as they contain chemicals of a non-naturally renewable source and are based upon a complex chemical manufacturing process. Hence there has been a desire to manufacture such absorbent structures without the use of significant amounts of thermoplastic materials, glues, binders or adhesives.

Whilst the above attempts describe various approaches to the above identified problems, it is believed that none of these absorbent structures leads to very performing absorbent articles. The absorbent capacity left unused and the complex manufacturing processes makes neither of the above absorbent articles technically, economically and/or environmentally advantageous.

Also, many prior art absorbent structures have a relatively homogeneous distribution of absorbent material in the main acquisition layer and/or storage layer and therefore exhibit a substantially homogeneous swelling in said area. For second, third and next liquid insults, these absorbent layers may act as a liquid barrier due to the fact that these absorbent materials generally lose on liquid uptake and/or absorption capability once they are at least partially wetted and in a certain liquid expanded swollen states. This results in slowing down and slowed down liquid absorption and distribution, which eventually leads to extra leakage.

The problem mentioned above typically arises in absorbent articles, such as disposable baby diapers, where the absorbent substance is an absorbent polymer material, which is excessively and substantially homogeneously and continuously distributed over a narrow crotch width. Typical high levels of absorbent polymer material (especially levels in excess of about 15-35%) as used in absorbent cores tend to induce a phenomenon referred to as "gel-blocking".

Gel-blocking occurs when the absorbent polymer material located in regions of first contact with fluid insults start to increase in volume as a consequence of imbibing the fluid, thereby forming a hydro-gel. When absorbent polymer material concentrations are high and wetted, the hydro-gel can block the initial and/or additional fluid from reaching other more absorbent regions of the absorbent core, thus leading to unappreciated, underused and/or unused absorbent capacity.

The occurrence of gel blocking and hydro-gelling can lead to too slow or limited liquid uptake, distribution and/or retention resulting in leakage during usage of the absorbent article. To remedy this problem, absorbent article designers have and typically use additional side cuffs, leakage barriers and/or acquisition and distribution layers which are expensive, inefficient and can only partly remedy these problems and limitations.

Hence, there is still an need in the art for an improved thin, flexible, lightweight absorbent structure for the use in an absorbent article which overcomes the problems of the prior art, which essentially comprises an absorbent structure with at least partially clustered, immobilized and/or restrained absorbent materials having effective and efficient fluid management during absorption, distribution and retention of bodily exudates. There is furthermore also a need for a method and apparatus to produce such absorbent structures at high production speed and low energy and raw material consumption.

Additionally, the present invention aims to provide improved absorbent structures, and elements for use therein, as well as absorbent articles utilizing such structures, utilizing integrated fluid management structures in and/or upon the absorbent core that effectively and efficiently absorbs the wearer's discharged body fluids upon initial and successive discharges, distributes and transports the absorbed liquid, from both initial and successive discharges over a relatively large proportion of the absorbent structure surface area, and allows for such discharged fluids to be effectively and efficiently stored.

SUMMARY

As a result of exhaustive research to address the above-identified, derived and related problems, the inventors have found that excellent fluid management can be achieved by absorbent structures, which will be explained in greater detail down below.

In particular, the present invention provides a substantially cellulose free absorbent structure for use in an absorbent article comprising:
 a) a carrier layer; and
 b) an auxiliary layer; and
 c) an absorbent material comprising absorbent polymer material provided between said carrier layer and said auxiliary layer; and
 d) attachments joining said carrier layer and said auxiliary layer together to at least partially immobilise the absorbent polymer material characterized in that the attachments are at least partially formed via a thermal, mechanical, thermo-mechanical and/or ultrasonic process An absorbent structure according to an embodiment of the present invention is characterized by improved liquid absorption, distribution and retention properties. The absorbent structure provided by the present invention is advantageous as it provides increased utilisation of absorbent materials within the absorbent core, such as absorbent polymer materials.

The absorbent structure according to the present invention is particularly useful to the personal hygiene industry (e.g. feminine hygiene garments, baby diapers and pants, adult incontinence garments) and many other industries and applications where it is desirable to work with flexible, thin, lightweight absorbent structures having improved efficiency and effectiveness for absorbing, distributing and/or retaining liquids. In a further aspect, the invention provides an absorbent article comprising an absorbent structure as provided by the invention. An absorbent article according to an embodiment of the invention has improved fit with discreet comfort.

In another aspect the present invention provides a method for the manufacturing of an absorbent structure for use in an absorbent article comprising the steps of:
 providing a carrier layer;
 covering the carrier layer with an absorbent material wherein said absorbent material comprises
  i) absorbent polymer material, and
  ii) from zero to an amount less than about 10 weight percent absorbent fibrous cellulosic material, based on the absorbent polymer material weight;

covering the absorbent material with an auxiliary layer which is joinable to the carrier layer; and joining the auxiliary layer to the carrier layer thereby forming attachments that define pockets there between wherein the absorbent polymer material is held in at least one of the pockets, characterized in that, the attachments are at least partially formed via a thermal, mechanical, thermo-mechanical and/or ultrasonic process.

Unlike previously existing absorbent articles and methods from the prior art limited by permanent or releasable immobilization and/or restraining means leading to unsatisfactory absorbency, distribution and retention parameters combined with limited flexibility, fit and wearing comfort, the present invention overcomes various problems relating thereto and deriving there from by having absorbent material containing compartments with pre-defined and well-managed permanent and detachable attachment grids.

More specifically the invention allows increased absorbent material expansion and swelling within the compartments, while additional distribution and transport arises within and in between the absorbent polymer material clusters which have until now been underused and unappreciated.

The present invention thereby does not only provide for an efficacious compartmentalization and restraining of absorbent materials in dry, partially and fully liquid loaded stated, it also allows a significant increase in efficiency and effectiveness of raw materials available in the absorbent structure within partially and fully liquid load state, increases overall absorbency and retention capacities and limits gel blocking, reduces rewet and minimizes leakage.

As a result of exhaustive research to address the above-identified, derived and related problems, the inventors have found that, based upon the same principles as described above, also excellent fluid and liquid management can be achieved by absorbent structures, which will be explained in greater detail down below.

In a preferred embodiment according to the present invention the absorbent structure comprises:

a) a carrier layer;

b) an auxiliary layer joined to the carrier layer to define at least one pocket there between for the containment of an absorbent material;

c) an absorbent material contained in at least one of the pockets, d) attachment means for attachment of the carrier layer to the auxiliary layer, the attachments comprising substantially permanent primary attachment means and substantially temporary secondary attachment means upon exposure of the absorbent structure to an amount of liquid, characterized in that, the attachments are provided and/or the absorbent material in the pockets were selected to provide that in a dry state the absorbent structure is of substantially equal thickness, and in a wet state, by means of the detachment of the substantially temporary secondary attachment means and/or differential swelling of the absorbent material in the compartments, the absorbent structure provides a liquid-managing surface structure.

An absorbent structure according to an embodiment of the present invention is characterized by improved liquid absorption, distribution, transport and retention properties, increased leakage prevention and lower rewet values. The absorbent structure according to an embodiment of the present invention is advantageous as it provides increased utilisation of absorbent materials within the absorbent structure, such as absorbent polymer materials and absorbent particulate polymer materials. Integrated fluid management as provided by an absorbent structure according to an embodiment of the invention delivers a more efficient usage of the available absorbent materials, resulting in thinner, flexible, lightweight absorbent articles with more effective and efficient absorbent structures, able to obtain a high absorbency performance and capable of handling relatively large amounts of discharged liquids also including multiple discharges of relatively large amounts of fluid in relatively short amounts of time. The absorbent structures according to an embodiment of the invention also allow absorbent articles with improved comfort, fit and discreteness.

Further advantageous features, aspects and details of the invention are evident from the dependent claims, the description and drawings as explained in more detail down below.

DETAILED DESCRIPTION OF THE INVENTION

Figure 1:
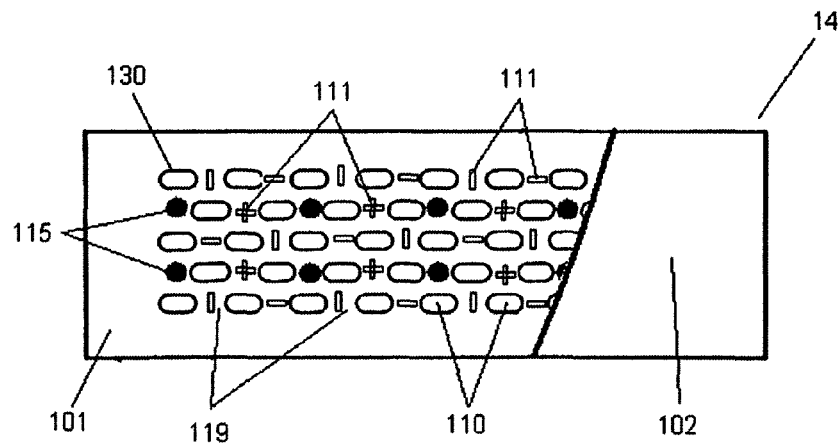
FIG. 1 provides a top view schematic illustration of an absorbent structure according to an embodiment of the invention.

The present invention concerns an absorbent structure for use in an absorbent product, preferably an absorbent article from the personal hygiene industry, such as feminine hygiene garments, baby diapers and pants and adult incontinence garments; and to a method and manufacturing of the same.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment", "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to absorb and/or retain bodily exudates.

"Absorbent component" as used herein refers to a structural constituent of an absorbent structure, e.g., a piece of an absorbent core, such as one of multiple pieces in a multi-piece absorbent core.

"Absorbent element" as used herein refers to a part of a functional constituent of an absorbent structure, e.g., a liquid acquisition layer, a liquid distribution layer, or a liquid storage layer formed of a material or materials having particular liquid handling characteristics suitable for the specific function.

"Absorbent insert" as used herein refers to a device adapted for insertion into an absorbent article and to serve as an absorbent structure when so inserted.

"Absorbent layer" as used herein refers to a term referring to a discrete, identifiable sheet-like or web-like element of an absorbent structure which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artefacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Acquisition layer", "acquisition region", "acquisition surface" or "acquisition material" and the like as used herein refer to a layer having a faster liquid uptake capability.

"Absorbency" is the ability of a material to take up fluids by various means including capillary, osmotic, solvent, chemical or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibres or particles in an air stream and condensing them from the air stream onto a moving screen by means of a pressure or vacuum; a web of fibres produced by airlaying is herein referred to an "airlaid"; an airlaid web bonded by one or more techniques to provide fabric integrity is herein referred to an "airlaid nonwoven".

"Apparent density", "density" as used herein refers to the basis weight of the sample divided by the calliper with appropriate unit conversions incorporated therein. Apparent density used herein has the unit $g/cm^3$.

"Attach", "attached" and "attachment" as used herein are synonymous with their counterparts of the terms "fasten", "affix", "secure", "glue", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "liquids" and the like as used herein are used interchangeably and refer to, but are not limited to urine, blood, vaginal discharges, breast milk, sweats and faecal matter.

"Binder", "adhesive", "glue", "resins", "plastics" and the like as used herein are used interchangeably and refer to substances, generally in a solid form (e.g. powder, film, fibre) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibres" as used herein refers to naturally occurring fibres based on cellulose, such as, for example cotton, linen, etc; wood pulp fibres are one example of cellulose fibres; man-made fibres derived from cellulose, such as regenerated cellulose (rayon), or partially or fully acetylated cellulose derivatives (e.g. cellulose acetate or triacetate) are also considered as cellulose fibres.

"Cluster" or the like as used herein refers to an agglomeration of particles and/or fibres.

"Chemically stiffened fibres", chemically modified fibres", "chemically cross-linked fibres", "curly fibres" and the like as used herein are used interchangeably and refer to any fibres which have been stiffened by chemical means to increase stiffness of the fibres under both dry and aqueous conditions, for example by way of addition of chemical stiffening agents (e.g. by coating, impregnating, etc), altering the chemical structure of the fibres themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight non-woven material used to contain and conceal an underlying absorbent core material; examples are the facing layer or materials that cover the absorbent cores of feminine hygiene garments, baby diapers and pants and adult incontinence garments.

"Crotch region" of an absorbent article as used herein refers to about 50% of the absorbent article's total length (i.e., in the y-dimension), where the crotch point is located in the longitudinal centre of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them insoluble.

"Diaper", "conventional diaper", "diaper-like", "diaper-like garment" and the like as used herein are used interchangeably and refer to disposable absorbent articles, which typically include a front waist portion and a back waist portion which may be releasably connected about the hips of the wearer during use by conventional fasteners such as adhesive tape fasteners or hook and loop type fasteners. In use, the article is positioned between the legs of the wearer and the fasteners are releasably attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Distribution layer", "distribution region", "distribution surface" or "distribution material" and the like as used herein are used interchangeably and refer to a layer having a larger capacity in wicking, dispersing and distributing liquids.

"Drylaying" as used herein refers to a process for making a nonwoven web from dry fibre; these terms apply to the formation of carded webs, as well as to the air laying formation of random webs; a web of fibres produced by drylaying is herein referred to as a "drylaid"; a drylaid web bonded by one or more techniques to provide fabric integrity is herein referred to a "drylaid nonwoven".

"Dry strength" as used herein refers to the strength of an adhesive joint determined in dry state conditions, immediately after drying under specified conditions or after a period of conditioning in the standard laboratory atmosphere.

"Fabric" as used herein refers to a sheet structure made from fibres, filaments and/or yarns.

"Feminine hygiene garments" as used herein refer to absorbent hygiene articles intended to be worn by woman, for absorbing and containing body exudates.

"Fibre" as used herein refers to the basic threadlike structure from which nonwovens, yarns and textiles are made. It differs from a particle by having a length at least 4 times its width; "Natural fibres" are either of animal (wool, silk), vegetable (cotton, flax, jute) or mineral (asbestos) origin, while "Man-made fibres" may be either polymers synthesised from chemical compounds (polyester, polypropylene, nylon, acrylic etc.) or modified natural polymers (rayon, acetate) or mineral (glass). "Fibre" and "filament" are used interchangeably.

"Fluff pulp" as used herein refers to wood pulp specially prepared to be drylaid.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the back sheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"Highloft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilisation layer" as used herein refers to a layer able to be applied to the absorbent polymer material or absorbent polymer material area with the intent to bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibres with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and faces the wearer facing layer; conversely, the term "lower" refers to the layer of the absorbent article which is nearest to and faces the garment facing layer. "Layer" is three dimensional structure with a x dimension width, y dimension length, and z-dimensions thickness or calliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibres by entangling them. This can be achieved by needling, stitching with fibres or by the use of high-pressure air or water jets and the like.

"Non-woven" as used herein refers to manufactured sheet, web or batt of directionally or randomly orientated fibres, bonded by friction, and/or cohesion and/or adhesion, excluding paper and products which are woven, knitted, tufted, stitch-bonded incorporating binding yarns or filaments, or felted by wet-milling, whether or not additionally needled. The fibres may be of natural or man-made origin and may be staple or continuous filaments or be formed in situ. Commercially available fibres have diameters ranging from less than about 0.001 mm to more than about 0.2 mm and they come in several different forms: short fibres (known as staple, or chopped), continuous single fibres (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Resin" as used herein refers to a solid or semisolid polymeric material.

"Substantially cellulose free" as used herein refers to an absorbent article, structure or core, that contains less than 20% by weight cellulosic fibres, less than 10% cellulosic fibres, less than 5% cellulosic fibres, no cellulosic fibres, or no more than an immaterial amount of cellulosic fibres which do not materially affect the thinness, flexibility or absorbency thereof.

"Thermobonding" as used herein refers to a method of bonding fibres by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localised heat through vibration thereby causing thermoplastic fibres to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibres produced by weaving is herein referred to as a "Woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fibre materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, non woven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibres by applying modified paper making techniques; a web of fibres produced by wetlaying is herein referred to as a "wetlaid".

"Wood pulp" as used herein refers to cellulosic fibres used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The recitation of numerical ranges by endpoints includes all numbers and fractions subsumed within that range, as well as the recited endpoints.

For reasons of optimal absorbency, distribution, retention, flexibility, fit, and/or comfort, it may be desirable for the absorbent material to substantially remain in its intended location in an absorbent structure.

Therefore, the present invention provides an substantially cellulose free absorbent structure for use in an absorbent article comprising:
   a) a carrier layer; and
   b) an auxiliary layer; and
   c) an absorbent material comprising absorbent polymer material provided between said carrier layer and said auxiliary layer; and
   d) attachments joining said carrier layer and said auxiliary layer together to immobilise the absorbent material characterized in that the attachments are at least partially formed via a thermal, mechanical, thermo-mechanical and/or ultrasonic process The present invention has also resulted from a realization that an absorbent article comprising a sandwich structure having compartments of absorbent material enveloped between a carrier layer and a auxiliary layer, can be more efficiently used to absorb, distribute and retain liquid, if certain bonds of the compartment pattern between the carrier layer and the auxiliary layer are able to loosen, dissolve, weakened and/or breakable when the absorbent structure is exposed to liquid while other bonds remain substantially unloosened, un-dissolved, unweakened and/or intact under the influence of wetted absorbent materials.

In particular, the present invention provides a substantially cellulose free absorbent structure for use in an absorbent article comprising:
   a) a carrier layer; and
   b) an auxiliary layer; and
   c) an absorbent material comprising absorbent polymer material provided between said carrier layer and said auxiliary layer wherein
     (i) substantially permanent primary attachments; and
     (ii) substantially temporary secondary attachments
   join said carrier layer and said auxiliary layer at least together characterized in that the attachments are at least partially formed via a thermal, mechanical, thermo-mechanical and/or ultrasonic process allowing the substantially temporary secondary attachments to be loosened as a result of exposing said absorbent structure to liquid whereas the substantially permanent primary attachments remain substantially intact.

Absorbent structures according to the present invention comprising a grid or pattern of attachment means throughout the absorbent structure which are able to loosen, dissolve or break under the influence of liquid, vapour and/or moisture and related absorbent material expansion provide the capability to firmly compartmentalize, immobilize and/or restrain absorbent material within the dry state while allowing additional increase by the individual and combined pockets during the wetting of the absorbent structure during normal usage conditions thereby creating additional space, volume and surface area in light of ongoing and continued expansion, swelling and/or loading of the absorbent material contained therein.

For reasons of optimal absorbency and/or retention, distribution and/or transport it may be desirable for the absorbent structure to have macroscopic surface structures such as heights and elevations and/or depressions and valleys which can act as channels, canals and/or embankments and guide the liquid in a desired manner. For reasons of optimal flexibility, fit, comfort and transportation and storage efficiency, it may be desirable for such macroscopic surface structures to appear and function only when needed, i.e. when the product is partially and/or fully wetted by liquid. The envisaged macroscopic surface structures are thus preferably not yet present prior to the usage of the absorbent structure.

The present invention also takes into account the realization that an absorbent article comprising a sandwich structure having absorbent material enveloped between a carrier layer and a auxiliary layer, can be more efficiently used to absorb, distribute, transport and retain liquid, if the absorbent structure is designed so as to exhibit an inhomogeneous swelling behaviour resulting in heights and elevations and/or depressions and valleys whereas it preferably remains substantially flat in a dry state, limited and/or only partially wetted state. It being understood that the absorbent structure can of course also posses already some less distinct form of macroscopic shape prior to wetting, preferably subsequently enhanced during the partial and/or full wetting of the absorbent structure by liquids.

In a particular embodiment, the present invention provides a substantially cellulose free absorbent structure comprising:
  a) a carrier layer; and
  b) an auxiliary layer; and
  c) an absorbent material comprising absorbent polymer material provided between said carrier layer and said auxiliary layer wherein
    (i) substantially permanent primary attachments; and
    (ii) substantially temporary secondary attachments
  join said carrier layer and said auxiliary layer at least partially together characterized in that the attachments are at least partially formed via a thermal, mechanical, thermo-mechanical and/or ultrasonic process allowing the substantially temporary secondary attachments to be loosened as a result of exposing said absorbent structure to liquid whereas the substantially permanent primary attachments remain substantially intact so as to provide the absorbent structure with a liquid-managing surface structure.

An absorbent structure according to the present invention is preferably characterized by bonds and/or joints designed to allow predetermined, controlled and/or gradual loosening, detaching and/or breaking of the attachment means within the pattern formed between the carrier layer and the auxiliary layer in line with the to be exerted forces generated by the absorbent material, preferably absorbent polymer material, within the absorbent structure when being loaded from a substantially dry to a partially loaded up to fully liquid loaded state.

The above described absorbent structure has for effect that the liquid which comes in contact with primary attachments, they primary attachment grids, will have no material impact on the structural integrity of said attachments and absorbent structure since they are substantially resistant during usage, while the liquids which come into contact with absorbent structure will influence the secondary attachments, the secondary pattern, by impacting the structural integrity of said attachments and pattern thereby allowing unprecedented functionalities. The clustered absorbent materials contained within pockets according to the invention will be allowed to increase in volume and size and/or combined to bigger compartments during usage, thus going beyond the initial dry pocket spaces and the bigger compartments are thus able to more freely take up further liquid due to the removal of initial restraining bonds and/or joints in between the carrier layer and auxiliary layer, while nevertheless they were securely and tightly in place the pre-usage stadium. This controlled unlocking of the absorbent material clusters during usage only, leads to several manufacturing, storage and transport advantages prior usage, since the absorbent materials can be position and clustered more accurately and effectively then before, which greatly improves fluid management in relation to absorption, adsorption, distribution and retention during usage. Obviously this leads to raw material savings and efficiency increase.

A preferred embodiment of an absorbent structure according to the present invention is characterized by a carrier layer and an auxiliary layer containing an absorbent material, preferably comprising an absorbent polymer material, there between whereby primary bonding regions and secondary bonding regions extending substantially from the wearer surface of the carrier layer to the garment surface of the auxiliary layer are provided such that the primary bonding region retains more integrity during and after absorption of liquids then the secondary bonding region under the same conditions. The difference in strength between the primary bonding regions and the secondary bonding region allows the carrier layer and auxiliary layer to separate in between said primary bonding regions, respectively at the secondary bonding regions, creating additional space and volume to allow further and free expansion of the absorbent material in the partially or fully liquid loaded state as opposed to the dry state. These secondary attachments, secondary attachment patterns and/or secondary bonding regions may but do not have to be wet-sensitive. The bonding strength should suffice the pre-usage and usage requirements of the particular absorbent structure.

While the dry immobilisation of the lower volume absorbent material is secured in the smaller pockets formed by the combination of the primary bonding regions and the secondary bonding regions, the wet immobilisation of the wetted higher volume absorbent material is still ensured by the bigger compartments defined by the enlarged and combined pockets as formed by the remaining primary bonding regions which are still substantially intact, after partial or full release of the secondary bonding regions during usage, being the influence of liquid, moisture and/or vapour imposed on the absorbent structure and its absorbent materials.

Ideally the liquid taken up by the absorbent material and the swelling and volume increase resulting there from is in line with the respective spaces and volumes created by the gradual, phased and incremental debonding and/or loosing process of the second bonding regions. This allows continuous immobilisation of the absorbent material without too little or too excessive restraining of the absorbent material due to too late or too early loosening of the secondary bonding regions during the loading, wetting and swelling process.

Hence, the absorbent structure will be designed so that the attachment means will be provided to at least partially immobilise and/or retain the absorbent material when the structure is dry, with the objective that the absorbent material remains at least partially restrained and/or immobilized when the absorbent structure is in a partially and/or fully wet condition. Since the absorbent material takes up liquid and swells, i.e. it gains in volume, it is thus important that the structure continuously encloses the absorbent material during the attachment means loosening process, without however restraining any such swelling due to too strong bonds and/or joint in the secondary bonding regions. Loosing the absorbent material coherence and integrity from dry to partially wet to fully wetted state will result in poor fluid management, leading to inferior, ineffective and/or failing absorbency, distribution and retention.

In a second aspect, the present invention provides an absorbent article comprising, at least in the front half of the absorbent article, an absorbent structure according to an embodiment of the invention. It is known that for most absorbent articles, for instance for articles such as feminine hygiene garments, baby diapers, baby pants and adult incontinence products, liquid discharge occurs predominantly in the front half. It is therefore advantageous to provide an improved absorbent article with an absorbent structure according to an embodiment of the invention in that area where fluid loading and uptake requirement is highest. Obviously, an absorbent article comprising an absorbent structure according to an embodiment of the invention which is entirely or partially located in either the front, crotch and/or back region of the absorbent article, such as for instance a baby diaper, is also covered under this invention. Any combinations thereof are hereby also encompassed.

In the hygiene industry, absorbent articles are specifically designed to absorb, distribute and retain bodily exudates. Apart from taking up liquid and retaining it within the absorbent structure of the absorbent article, the absorbent articles are also intended to satisfactory prevent bodily exudates from soiling, wetting, or otherwise contaminating clothing or other articles, such as bedding, that may possibly or come in contact with the wearer. A disposable absorbent article, such as a disposable diaper, may be worn for several hours in a dry state and/or in liquid loaded state. Accordingly multiple attempts have been made toward improving the fit and wearing comfort of the absorbent article, both when the article is dry and when the absorbent article is fully or partially loaded with bodily exudates, while enhancing the absorption, distribution and retention functions of the absorbent article. Obviously flexible, thin, light-weight and discreet absorbent articles are also here greatly preferred.

The absorbent article according to an embodiment of the invention comprises a liquid-permeable top sheet, a liquid-impermeable back sheet, and an absorbent storage layer immobilised and/or restrained in between an auxiliary layer and carrier layer. It being understood that either the carrier layer and/or the auxiliary layer can directly or indirectly act as immobilisation, liquid permeable distribution or impermeable layer, either unitary, separately or as a combination, within the absorbent structure and/or absorbent article. The primary bonding regions and the secondary bonding regions define compartments wherein clusters of absorbent material are held in the compartments.

Absorbent articles according to a preferred embodiment of the invention contain an absorbent material such as for instance absorbent polymer material, more preferably absorbent particulate polymer material. It is known when absorbent polymer material absorbs liquid and swells it performs more effective and efficient when disposed in a certain pattern or arrangement (cfr. gel-blocking). The predefined locations and dosing of the absorbent particulate polymer materials is intended to obtain optimal absorbency, fit and/or comfort. Since it is desirable for absorbent particulate polymer material to remain in its intended location and thus avoid migration and uncontrolled movement thereof within the absorbent article and/or absorbent structure, the absorbent material is desirably immobilized and/or restrained via the absorbent structure in such a way that the absorbent particulate polymer material performs both in partially liquid loaded as well as in fully liquid loaded condition. Hence continued immobilisation is very much preferred.

In addition to being absorbent, absorbent articles are desirably thin, light and flexible; for fit, ease and comfort during use but also for more convenient, economical, environmental and neat packaging, transport and storage in for instance warehouses, stores and end-consumer accommodations. Absorbent articles, which are often used in large quantities, are also desirably inexpensive. Some prior art technologies of immobilizing absorbent polymer material in absorbent articles add bulk to the absorbent article and thereby increase thickness and weight, reduce flexibility and raise the cost and environmental footprint of the absorbent article. Other technologies for immobilizing absorbent polymer material in an absorbent article may not be as effective in maintaining immobilization when the absorbent article is wetted in comparison to the initial dry state and may therefore lead to less effective and less efficient usage of the absorbent materials incorporated therein due to for instance gel blocking and physical or chemical isolation of said raw materials. There remains a need for a method to continuously immobilise and/or restrain the absorbent material within the absorbent structure before, during and after the transitioning from an initially dry to an ultimately fully wetted absorbent article which is flexible, thin, light-weight, discreet and/or inexpensive while preserving required absorption, transport and retention functions.

In a preferred embodiment, the absorbent article comprises an absorbent structure comprising a carrier layer and auxiliary layer, whereby the upper surface of the carrier layer is facing the wearer's skin and a lower surface of the auxiliary layer is facing the garment of the wearer. The absorbent material is preferably in direct contact with the lower surface of the auxiliary layer and the upper surface of the carrier layer, however additional fabric, non-woven, woven, tissue and/or paper layers can be provided to accommodate fluid management and integrity. The absorbent materials are preferably clustered and encapsulated by a plurality of smaller pockets as formed by the primary bonding regions and secondary bonding regions. The absorption layer typically has an absorbing capacity of at least about 100 $g/m^2$, preferably at least about 200 $g/cm^2$, more preferably at least about 600 $g/cm^2$, most preferably at least about 700 $g/cm^2$.

In a preferred embodiment of an absorbent article according to the present invention, the absorbent material clustered in the pockets defined by the bonds and/or joints of the primary bonding regions and/or secondary bonding regions of the carrier layer and auxiliary layer comprises at least absorbent polymer material. In a more preferred embodiment of the absorbent structure of the invention, the absorbent material comprises a super absorbent polymer (SAP), and more preferably a highly permeable absorbent particulate polymer material is present in the absorbent material in an average basis weight of at least about 100 $g/m^2$, preferably at least about 200, more preferably at least about 400, even more preferably at least about 600, most preferably at least about 700 $g/m^2$. Use of a super absorbent polymer as absorbent material provides an improved absorption.

The bonding strength, such as for example the dry strength, wet burst strength and/or wet strength, should suffice the required parameters of the absorbent structure and will amongst others depend on the absorbent article, its product size and shape and the required duration of the usage and performance. The specific structural and functional strength of the bonds and joints in between the auxiliary layer and the carrier layer and the different wet strengths in between the bonds and/or joints of the primary bonding regions and the secondary bonding regions allows for more efficient design and usage of the absorbent structures leading to more, faster and enhanced absorption, distribution and retention of liquids, such as bodily exudates. Moreover it also allows for better and controlled liquid wicking and dispersion within said absorbent storage layer, leading to more efficient and effective fluid communication or transport from the less absorbent area's (e.g. saturated) to the more absorbent area's (e.g. unsaturated).

It is noted that when stated that liquids comes into contact with the absorbent structure and absorbent materials and the primary attachments suffer no material impact on their structural integrity, e.g. they remain substantially intact, reference is preferably being made to characteristics of such absorbent articles, absorbent structures and/or attachments under relatively normal wearing/usage conditions, typical usage timing, average liquid amounts and intervals at room or body temperatures without taking into account exaggerated, severe and/or extreme conditions such as for example abnormal large amounts of liters of liquid during multiple days of intense contact. In such case, although not preferred, the initially resistant primary attachments, might become loosened, detached or broken up after all. It would be clear from the above that such primary attachments eventually turning into secondary attachments after being exposed to prolonged and/or more intense usage conditions are also envisaged under this invention.

In a third aspect, an absorbent structure according to an embodiment of the invention is used in a feminine hygiene garment, baby diaper, baby pants or adult incontinence garment product. While particular embodiments of the present invention have been illustrated and described, it would be obvious to those skilled in the art that various other changes and modifications can be made without departing from the spirit and scope of the invention.

Examples are used below for further non-limitative illustration of the invention.

Figure 2:
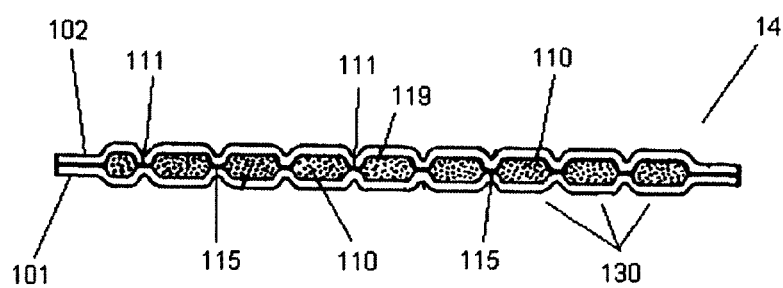
FIG. 2 provides a cross-sectional schematic illustration of an absorbent structure according to an embodiment of the invention.

With reference to FIG. 1 and FIG. 2, the absorbent structure 14 includes at least one carrier layer 101 and at least one auxiliary layer 102, and absorbent material 110. The carrier layer 101 and auxiliary layer 102 are attached to each other in primary bonding regions 111, optionally via a primary attachment medium 112. The carrier layer 101 and auxiliary layer 102 are also attached to each other in secondary bonding regions 115, optionally via a secondary attachment medium 116. Apart from the primary bonding regions 111 and secondary bonding regions 115, there are also unattached regions 119, where there is substantially no bond and/or joint between the carrier layer 101 and auxiliary layer 102, thereby providing a plurality of pockets 130 in which an absorbent material 110 can be located to form a cluster of absorbent material 110. The primary bonding regions 111 correspond with a primary bonding grid 113, whereas the secondary bonding regions 115 correspond with a secondary bonding pattern 117.

As carrier layer 101 and/or auxiliary layer 102, one can choose from a variety of materials such as but not limited to a non-woven or a woven fabric, a wetlaid material such as cellulose tissue, paper, a film, a tissue, a perforated film, a foam material, a thermoplastic material, a layer of adhesive or whatever material suitable within the absorbent structure 14. These layers can have a basis weight in the range from 3-400 gsm. Carrier layer 101 and auxiliary layer 102 can be made out of the same material or can have different compositions, weights and/or structures. In a preferred embodiment of this invention, at least one of the layers is liquid permeable over at least part of its surface so that liquids can be taken up in the Z-direction. In another preferred embodiment both the carrier layer 101 and the auxiliary layer 102 are liquid permeable. In yet another preferred embodiment, one of the layers is a liquid permeable non-woven material and the other layer is a substantially liquid-impervious and possibly breathable PE film, whereby the non-woven is positioned at the expected liquid flow such as the wearer-facing side of the absorbent structure 14 in case of an absorbent article such as a baby diaper, and the PE film is positioned away from the expected liquid flow such as the garment-facing side of the absorbent structure in case of an absorbent article such as a baby diaper. In this case, one could select for instance a 22 gsm polypropylene non-woven material from Albis, Italy and a 20 μm breathable polyethylene film from Nuova Pansac, Italy. The use of the terminology 'carrier layer' by no means implies that the fabric should be strong enough to support the structure or should be situated at the lower region of the absorbent structure 14. Nor does 'auxiliary layer' imply that this layer should have a lesser function or should by analogy be situated at the upper region of the absorbent structure 14.

The pockets 130 can have a regular shape, irregular shape or combination thereof. Preferred shapes of the pockets 130 are circular, elliptic or square with a diameter, radius or side larger than about 0.1 mm, 0.2 mm, 0.3 mm, 0.4 mm, 0.5 mm, more preferably larger than about 0.75 mm and smaller than about 60 mm, more preferably larger than about 1.0 mm and smaller than about 40 mm and most preferably larger than about 2.00 mm and smaller than about 10 mm. At least one of the pockets 130 contains absorbent material 110. For absorbent article applications, such as a diaper or pant, the absorbent material 110 preferably contains an absorbent polymer material, more preferably absorbent particulate polymer material as also known in the art. Such absorbent polymer materials are for instance offered by Evonik from Germany, BASF from Belgium and Nippon Shokubai from Japan. The absorbent polymer material can form 100% of the absorbent material 110 or it can be used in combination with other absorbent materials such as for instance cellulose fibres or fluff pulp.

Figure 3:
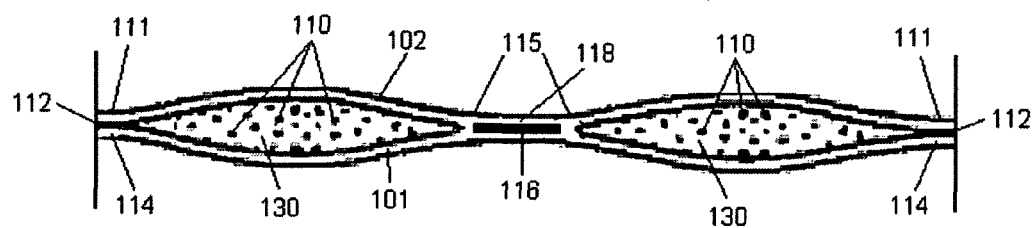
FIG. 3 provides a cross-sectional schematic illustration of an absorbent structure in an dry intact state according to an embodiment of the invention.

With reference to FIG. 3 the absorbent material 110 is distributed in between the carrier layer 101 and the auxiliary layer 102 along an absorbent material pattern. The absorbent material pattern from the absorbent structure 14 can be random or regular, substantially continuously connected or isolated, fully-covering or partially covering and/or any other suitable pattern. In a preferred embodiment, the absorbent material 110 is regularly and continuously patterned to allow for a good and controlled liquid absorption, distribution and retention. Even more preferably, the absorbent material 110 pattern consists of several clusters of absorbent material 110, surrounded by areas where substantially no absorbent material is present, which can act as distribution and transport channels facilitating the flow and/or mass flow of liquid away from the point of insult and towards various clusters of absorbent material 110. In general, the weight distribution of absorbent material 110 over the absorbent structure 14 can be regular across the major surface or can profiled, i.e. the basis weight of the absorbent material 110 may change depending on its position in the absorbent structure 14. Such profiled distribution of absorbent material 110 is very useful in e.g. diaper and pants cores where one would like to concentrate absolute and/or relative more absorbent material 110 near the point of liquid insult, such as for instance at the front region of an absorbent article.

The pocketed absorbent material 110 does not necessarily fill the pockets 130 entirely as it might be advantageous to leave some void space adjacent the absorbent material 110 in the pockets 130 or leave some pockets 130 partially or completely empty. For certain absorbent articles or absorbent structures 14, it can be useful to also provide absorbent material 110 in at least part of the primary bonding regions 111 and/or secondary bonding regions 112.

Figure 4:
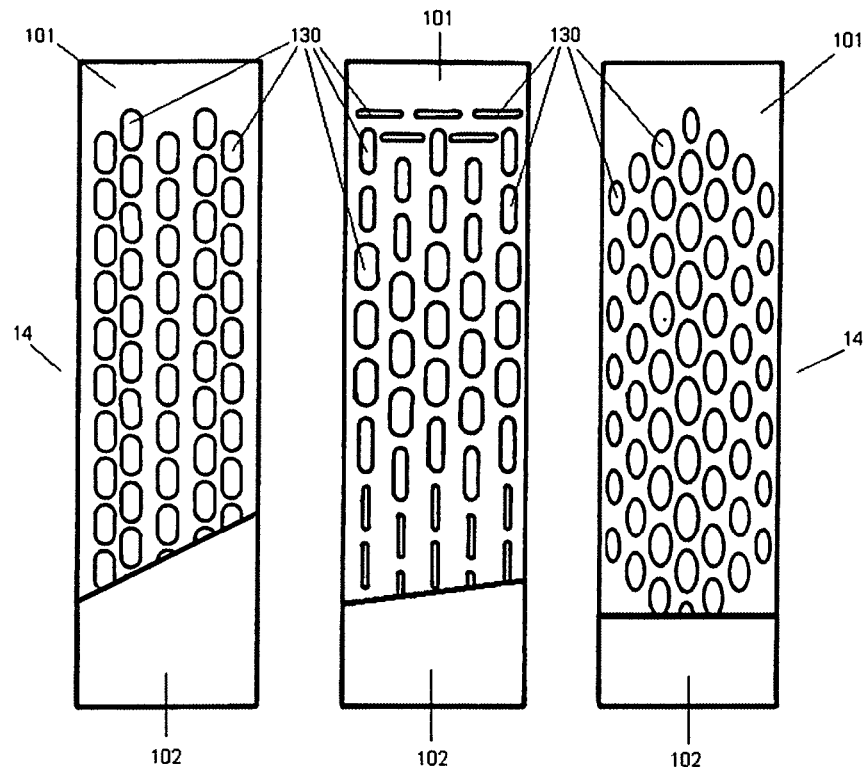
FIG. 4 provides a top view schematic illustration of absorbent structures according to embodiments of the invention.
Figure 4:
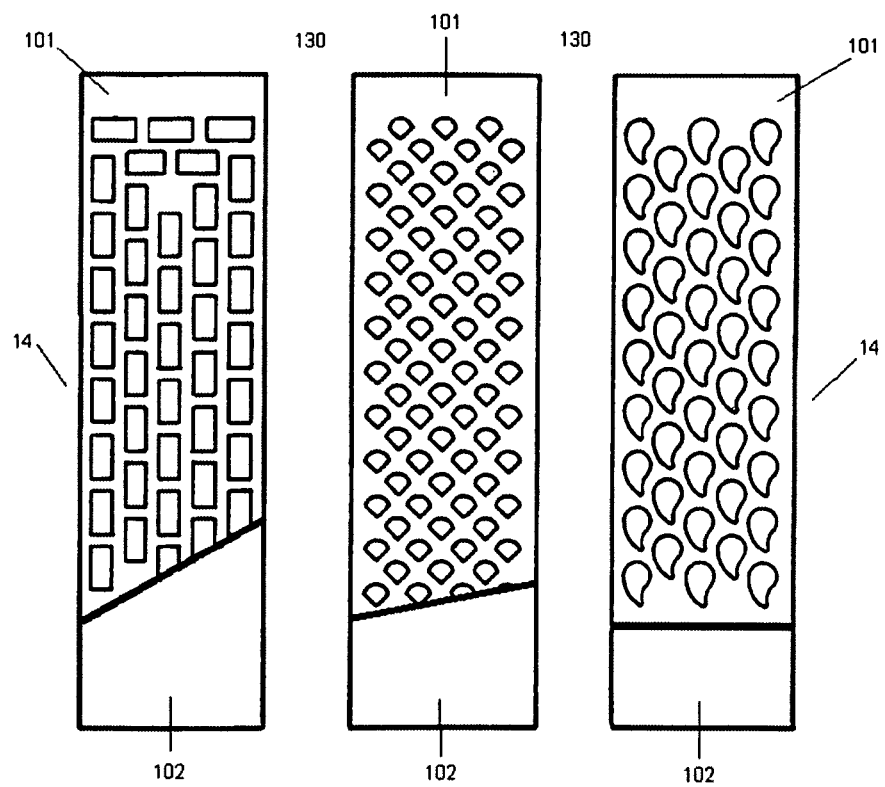

With reference to FIG. 4, the carrier layer 101 and auxiliary layer 102 are attached to each other in primary bonding regions 111, optionally via a primary attachment medium 112, and they are also attached to each other in secondary bonding regions 115, optionally via a secondary attachment medium 116. Typical examples of methods used to bond or join materials to each other are by way of example, but are not limited to, the use of an adhesive such as for instance pressure sensitive adhesive, curing, via a chemical links such as for instance hydrogen bonds or via the use of ultrasonic and/or other thermal, mechanical? thermo-mechanical OR chemical bonding techniques such as for instance heat sealing, needling, air and water jet pressure, and the like. In case an additional material next to the carrier layer 101 and auxiliary layer 102 is used to bond or join both layers to each other, such as an adhesive, glue or binder, then said additional material, in this case for instance the adhesive substance, acts as the attachment medium. The adhesive substance acting as bonding or joining agent within the primary bonding regions 111 is called the primary attachment medium 112, and the adhesive substance acting as bonding or joining agent within the secondary bonding regions 115 is called the secondary attachment medium 116. However, if the carrier layer 101 and the auxiliary layer 102 are solely attached to one another for example via an area of mechanical resistance or entanglement, or via an area on which the layers are fused together; without the need of any additional bonding or joining agent, no attachment media is provided.

Several known prior art products use thermoplastic, adhesive, glue and/or binder as attachment medium. It is the objective of the present invention however to preferably work without the use of thermoplastic, adhesive, glue and/or binder as attachment medium and/or immobilization layer for technical, economical and/or environmental reasons. In a preferred embodiment of this invention, ultrasonic bonding and/or thermosealing is used to create the attachments, hence essentially alleviating the need for excessive attachment media or agents.

The effective bonds or joint, with or without presence of bonding or joining agents, are respectively referred to as primary attachments 114 in the primary bonding regions 111 and secondary attachments 118 in the secondary bonding regions 115.

In the primary bonding regions 111 the primary attachments 114 are designed to maintain the integrity of the absorbent structure 14 when it is substantially dry, but also when it is and/or has been wetted and is partially or fully loaded with liquid. The primary bonding regions 111 thus have to substantially resist the frictions and strain during normal use of the absorbent article and the forces resulting from the expanding and swelling absorbent material 110 caused by the liquid uptake. This means that some of the attachments between the carrier layer 101 and the auxiliary layer 102 will substantially remain intact if the absorbent article is in use and/or is being wetted. Preferably the separation force necessary to release the other attachments in between the carrier layer 101 and auxiliary layer 102 will be higher than about 0.05 N/cm or about 0.75 N/cm, more preferably higher than about 0.1, N/cm, 0.2 N/cm or 0.3 N/cm, even more preferably higher than about 1.0 N/cm, 1.5 N/cm, 2.5 N/cm and most preferably higher than about 3-5 N/cm.

Various methods of attaching two materials, layers or components together are known in the art. In a preferred embodiment, the primary attachments 114 and secondary attachments 118 are thermo-sealings. The thermo-sealing areas of the primary bonding regions 111 being relatively large(r) in surface, tenacity or integrity (than the thermo-sealing area's of the secondary bonding regions 115), resulting in a absolute or relative high(er) separation force. In general, the attachments can come in various sizes and shapes, but it is preferred to provide them with rounded edges to inhibit the carrier layer 101 and auxiliary layer 102 from tearing apart. It is also preferred to design the attachment so that they have an average surface size of at least about 0.5 mm$^2$, preferably at least about 1.0 mm$^2$, 2 mm$^2$ or 3 mm$^2$, more preferably at least and most preferably at least about 16 mm$^2$. Also the density of the attachments can vary, depending on the surface size of the individual attachments and the desired separation forces. For attachments with a surface area smaller than 1 cm$^2$ for instance, it is preferably recommended to use a density of at least about 100 per m$^2$.

Making the attachment areas in a round, elliptic or square shape can have some advantages, such as a reduced investment cost in the required tooling. However, for certain applications and to further reinforce the attachments and the resulting separation force, it can be advantageous to design extended attachment areas, i.e. attachment areas in a shape having a major axis length and a shorter minor axis width. If the forces resulting from normal use of the absorbent article and from the swelling of the absorbent material 110 would come from different directions, then the attachment areas would be oriented to cope with these forces, e.g. by providing a pattern of longitudinal-shaped attachments where for instance some of the attachments have a longitudinal axis which is perpendicular to the longitudinal axis of some of the other attachments.

Figure 5:
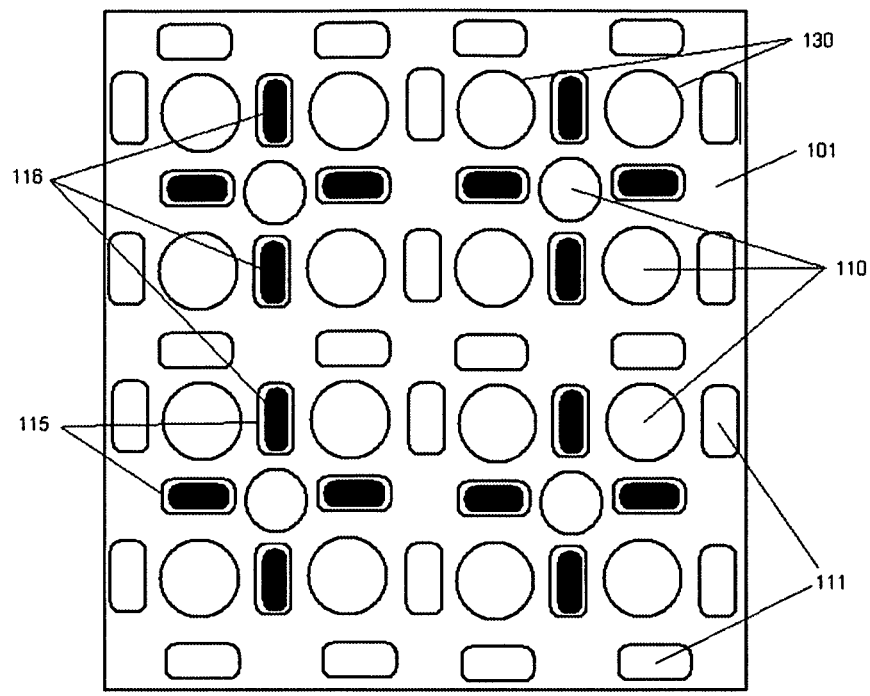
FIG. 5 provides a top view schematic illustration of an absorbent structure according to an embodiment of the invention.
Figure 6:
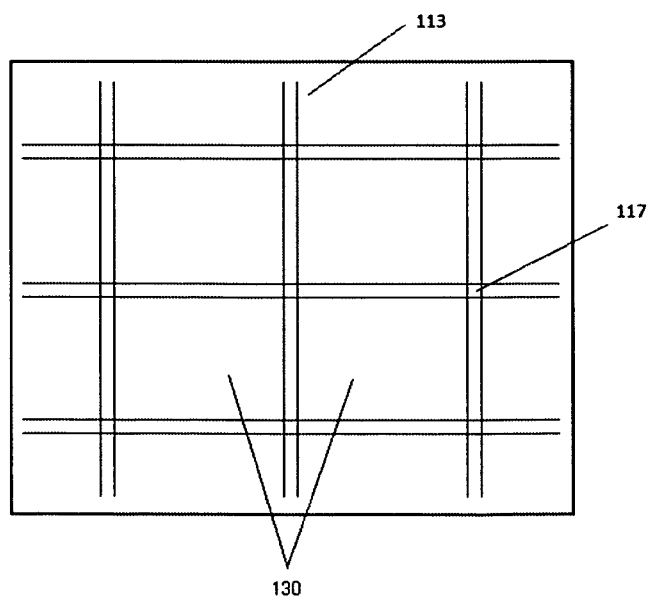
FIG. 6 provides a top view schematic illustration of an attachment grids and patterns according to an embodiment of the invention.

In a preferred embodiment, the primary bonding regions 111 of the absorbent structure 14 are arranged in a grid consisting of rounded elements of which around 50% are oriented along an X-axis, and the remainder along a Y-axis, an example of which can be seen in FIG. 5. In another embodiment of this invention, the primary attachments 114 are arranged in a primary bonding grid 113 composed of continuous lines in a grid, a example of which can be seen in FIG. 6 so as to allow for easy liquid distribution and transport, for a high separation force and high resistance against the propagation of an eventual crack or fissure in one of the pockets 130. The primary bonding grid 113 is carefully designed so that in a wetted state, the swollen material remains stabilized around the locations where it was restrained and/or immobilized in its dry state. Failure to do so would result in breaking-up and/or displacement of the wet absorbent material, resulting in loss of absorbent performance, reduced fit and comfort and even product failure leading to poor fluid management within the absorbent structure.

The secondary attachments 118 in the secondary bonding region 115 are designed to release when the absorbent article is being wetted. Preferably the secondary attachments 118 will break under influence of the forces resulting from the expansion and swelling of the absorbent material 110 when it is sufficiently wetted. This implies for most of the standard absorbent materials 110 that the secondary attachments 118 should have a relative low separation force when wet, however wet-sensitivity is not required. Preferably the separation force necessary to break the secondary attachment 118 will be lower than about 5.0 N/cm, more preferably lower than about 1.0, 2.0 or 2.5 N/cm, even more preferably lower than about 0.75, 0.5 or 0.25 N/cm and most preferably lower than about 0.20 or 0.10 N/cm when wet. In a preferred embodiment of this invention, both layers are thermo-sealed together, the thermo-sealing areas of the secondary bonding regions 115 being relatively small(er) in surface, tenacity or integrity (than the primary bonding regions 111) resulting in a absolute or relative low(er) separation force. The thermo-sealing areas can come in various sizes and shapes, but it is preferred to provide at least one sharp edge to facilitate the carrier layer 101 and auxiliary layer 102 to tear apart. It is advantageous to use thermo-sealing as attachment means, rather than using adhesive and/or glues as the production cost is then usually substantially lower and one can claim to be 'adhesive-free' or 'glue-less', a claim which is important to environment-conscious consumers and results in less expensive end products.

The shape of the primary attachments 114 and secondary attachments 118 may change throughout the absorbent structure 14, i.e. it is not necessary for all primary attachments 114 and/or secondary attachments 118 to have the same shape, but both can vary according to the requirements in that part or region of the absorbent article. In the embodiment shown in FIG. 1, the primary attachments 114 for instance are made up by elliptical-like shapes, such as uni-dimensional and bi-dimensional elliptical shapes. The secondary attachments 118 for instance are made up by round and/or dot shapes.

Figure 7:
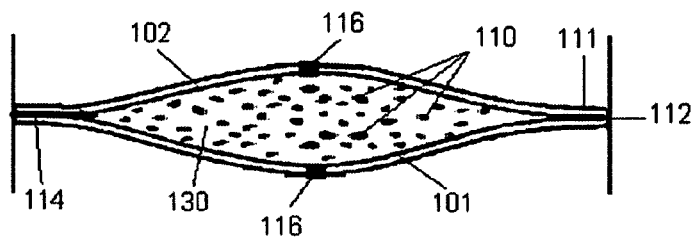
FIG. 7 provides a cross-sectional schematic illustration of an absorbent structure in partially wetted state according to an embodiment of the invention, indicating primary attachments and secondary attachments.
Figure 8:
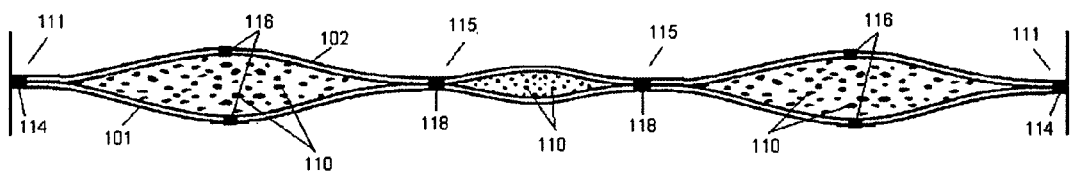
FIG. 8 provides a cross-sectional schematic illustration of an absorbent structure in partially wetted state according to an embodiment of the invention, showing phased expansion to reduce side leakage.

As can be seen in FIGS. 7 and 8, the breaking of the secondary attachments 118 in the secondary bonding regions 115 allows the carrier layer 101 and/or auxiliary layer 102 to deform, stretch and/or change shape. As a result, the minimum volume pockets are able to expand to a combined maximized volume compartment 124 so as to accommodate at least part of the extra volume resulting from the expanding absorbent material 110. Thus, an absorbent structure 14 for usage in an absorbent article with expandable pockets is created, allowing the absorbent material 110 to be more effectively and efficiently used and reducing the risk of bursting of either or both of the carrier layer 101 and/or auxiliary layer 102. The extra volume created by the expanding pockets can be about 1% to 5% of the original volume. Preferably it is higher than about 5% to 25%, more preferably higher than about 25% to 50%, most preferably higher than about 50% or 100% of the original volume.

In a preferred embodiment, the secondary bonding regions 115 consist of various sub-regions, corresponding with different separation forces. It is thus possible for the one skilled in the art to design an absorbent structure 14 with a gradual, controlled and/or phased expansion.

Figure 9:
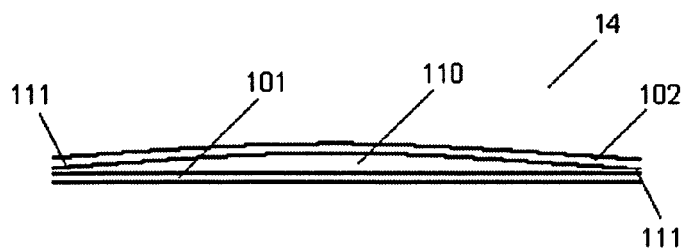
FIG. 9 provides a cross-sectional schematic illustration of an absorbent structure in its dry state according to a prior art embodiment.
Figure 10:
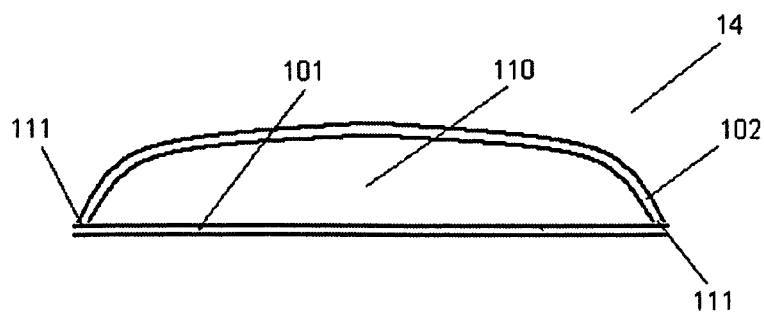
FIG. 10 provides a cross-sectional schematic illustration of an absorbent structure in its wetted state according to a prior art embodiment.

With reference to FIGS. 9 and 10 illustrating prior art, the absorbent structure 14 includes at least one carrier layer 101 and at least one auxiliary layer 102, and absorbent material 110. The carrier layer 101 and auxiliary layer 102 are attached to each other in primary bonding regions 111, optionally via a primary attachment medium 112. When liquid is applied, the structure starts to swell in a substantially homogeneous manner until the available liquid uptake capacity by the absorbent material is reached and/or the available free space within the absorbent structure 14 is taken up by the swollen and volume-expanded absorbent materials 110. As there is no macroscopic i.e. larger scale superficial three-dimensional liquid management structure present, there is a high risk of creating side leakage and/or a necessity to provide absorbent article containing such absorbent structure 14 with additional and complex superficial and/or side barrier or flap structures.

Figure 11:
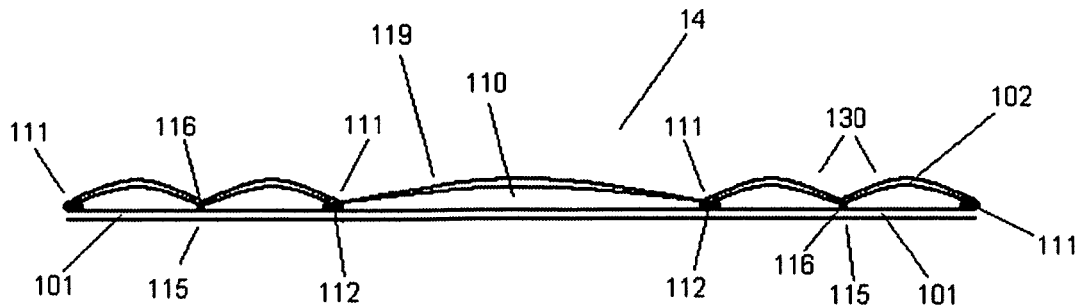
FIG. 11 provides a cross-sectional schematic illustration of an absorbent structure in dry state according to an embodiment of the present invention.
Figure 12:
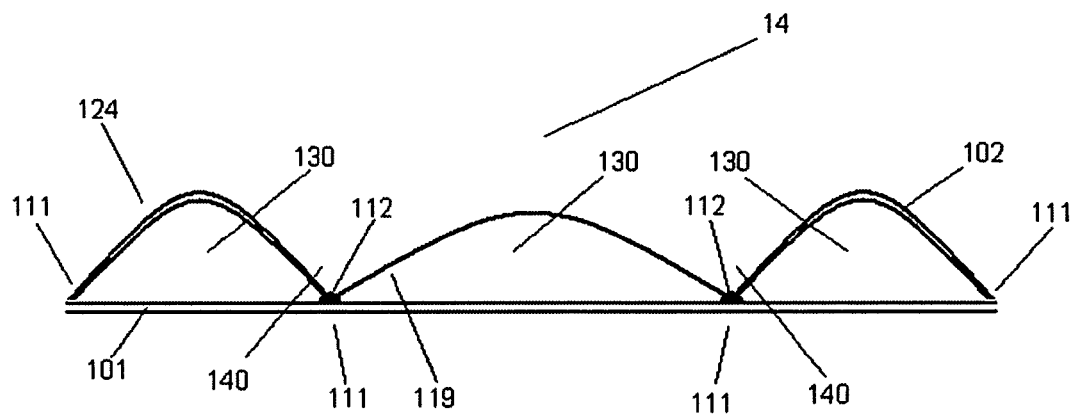
FIG. 12 provides a cross-sectional schematic illustration of an absorbent structure in wetted state according to an embodiment of the present invention.
Figure 13:
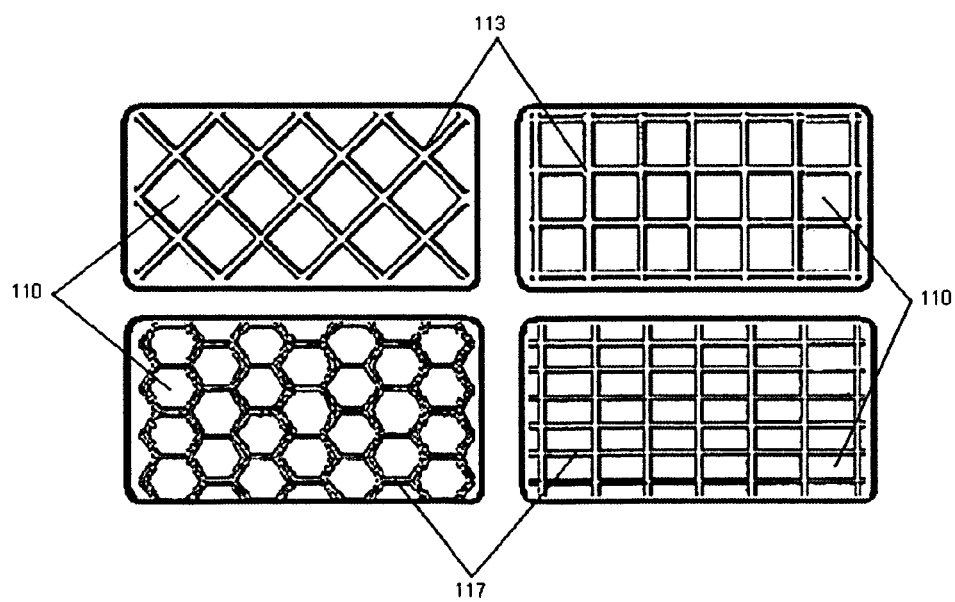
FIG. 13 provides a top view schematic illustration of a primary bonding grids and secondary bonding patterns according to embodiments of the invention.

With reference to FIGS. 11 and 12, the absorbent structure 14 includes at least one carrier layer 101 and at least one auxiliary layer 102, and absorbent material 110. The carrier layer 101 and auxiliary layer 102 are attached to each other in primary bonding regions 111, optionally via a primary attachment medium 112. The carrier layer 101 and auxiliary layer 102 are also attached to each other in secondary bonding regions 115, optionally via a secondary attachment medium 116. Apart from the primary bonding regions 111 and secondary bonding regions 115, there are also unattached regions 119, where there is substantially no bond and/or joint between the carrier layer 101 and auxiliary layer 102, thereby providing a plurality of pockets 130 in which an absorbent material 110 can be located to form a cluster of absorbent material 110. With reference to FIG. 12, depicting FIG. 11 in a wetted and swollen state, it is obvious that primary bonding regions 111 will act as liquid-guiding 'channels', whereas secondary bonding regions 116 will act as liquid-resisting 'embankments', thus forming a macroscopic liquid management surface structure As can be seen in FIG. 12, the loosening, detachment and/or breaking of the secondary attachments 116 in the secondary bonding regions 115 allows the carrier layer 101 and/or auxiliary layer 102 to deform, stretch and/or change shape. As a result, the minimal volume pockets 122 are able to expand to an intermediate volume and further to a maximum compartment pocket 124 so as to accommodate at least part of the extra volume resulting from the expanding absorbent material 110. Thus, an absorbent structure 14 with heights in areas 130 and depressions in areas 140 is created. The depressions in areas 140 can act as canals, draining the liquids towards desired areas in the absorbent structure 14. The heights in areas 130 can act as barrier, obstacles or embankments, draining the liquids away from undesired areas in the structure. The extra volume created by the expanding pockets can be about 1% to 5% of the original volume. Preferably it is higher than about 5% to 25%, more preferably higher than about 25% to 50%, most preferably higher than about 50% or 100% of the original volume.

Figure 14:
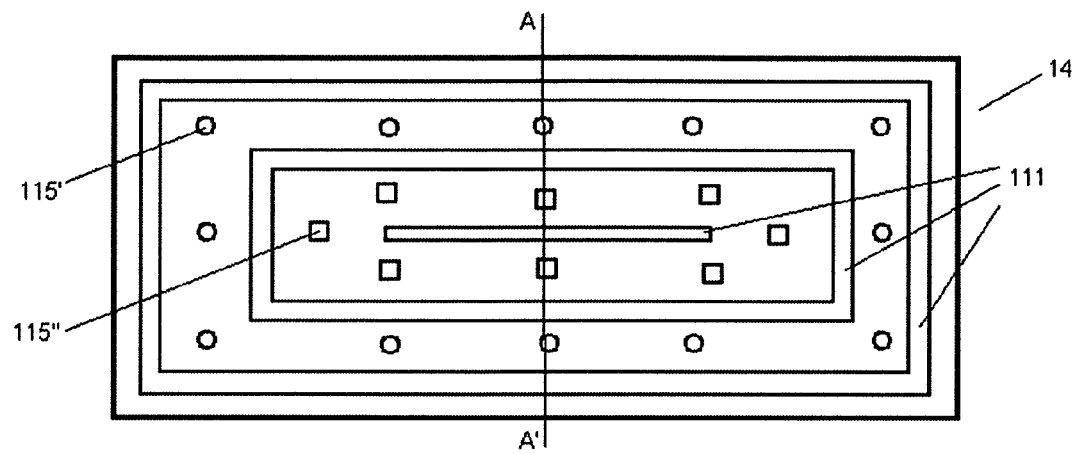
FIG. 14 provides a top view schematic illustration of an absorbent structure according to an embodiment of the present invention, illustrating phased expansion.
Figure 15:
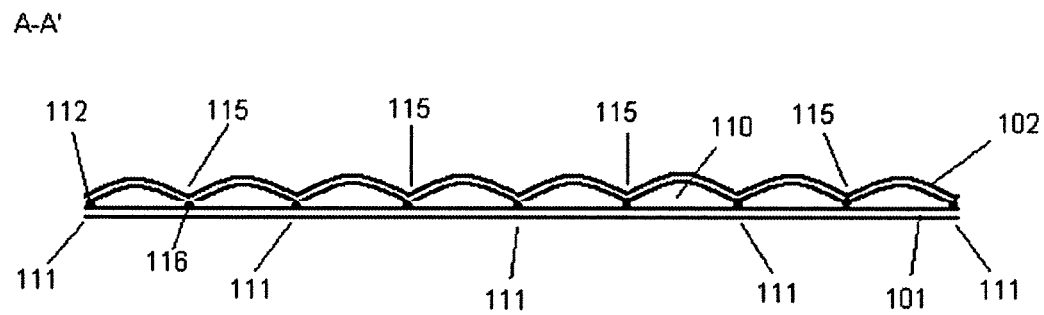
FIG. 15 provides a cross-sectional schematic illustration of the absorbent structure of FIG. 13 in dry state according to an embodiment of the invention.
Figure 16:
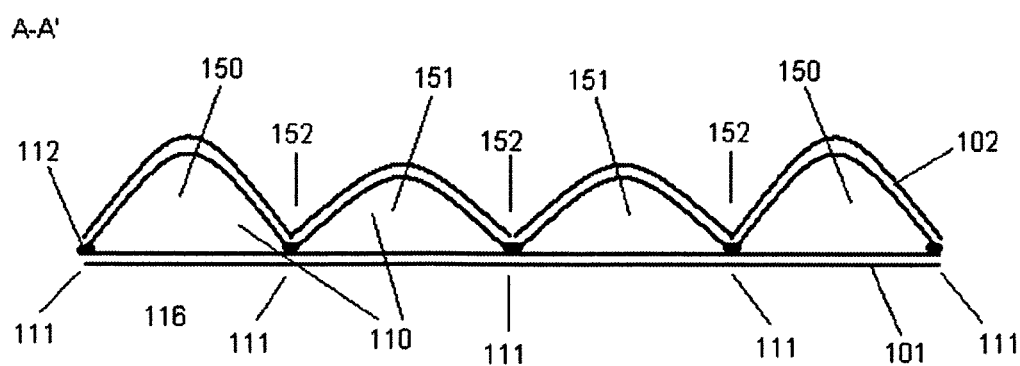
FIG. 16 provides a cross-sectional schematic illustration of the absorbent structure of FIG. 15 in wetted state according to an embodiment of the invention.

In a preferred embodiment, the secondary bonding regions 115 consist of various sub-regions, corresponding with different separation forces. FIGS. 14, 15 and 16 show exemplary embodiments according to the invention are where secondary bonding regions 115 consist of weaker secondary bonding regions 115' and stronger secondary bonding regions 115" where weaker secondary bonding regions 115' loosen faster than the stronger secondary bonding regions 115". The different functionalities in between the primary bonding regions 111 and secondary bonding regions 115 in combination with the bonding strength differentiation in between weaker secondary bonding regions 115' and stronger secondary bonding regions 115" allows the design of an absorbent structure 14 with a predetermined, controlled and/or phased volume-expansion of the absorbent structure. In a more preferred embodiment, the absorbent structure 14 consists of weaker secondary bonding regions 115' at the periphery of the absorbent structure 14 allowing for primary and easy expansion of the absorbent material 110 adjacent the longitudinal and/or end edges of the absorbent structure 14, thereby creating containment or anti-leakage barriers within the absorbent structure 14. Such a particular internal incorporated barrier construction has great pre-usage, usage and post-usage advantages for the construction of diapers or pants. As shown in FIGS. 14, 15 and 16, the weaker secondary bonding regions 115' loosen to form first barriers or embankments 150, whereas the stronger secondary bonding regions 115" form the only later arising secondary barriers or embankments 151.

The resistant primary bonding regions 111 form canals 152 in between the first embankments 150 and/or the secondary embankments 151. Due to the time difference between the formation of the first embankments 150 and the respective secondary embankments 151, the first embankments 150 will contain the liquid inside the product, where it can be distributed via the canals 152 and it will further be stored in and contained by secondary embankments 151. Obviously various combinations are possible.

In another preferred embodiment, at least one of the carrier layers 101 or auxiliary layer 102 is made out of an elastic or stretchable material, allowing for at least a first volume expansion before the gradually increasing expansion force of the wetting and swelling absorbent materials 110 accommodates the eventual breaking of the wet secondary attachments 118.

In an alternative preferred embodiment, the absorbent structure 14 consists of a multilayered sandwich structure where on the first sandwich structure of carrier layer 101—absorbent material 110—auxiliary layer 102, additional layers of absorbent 110 material and/or complementary layers have been added. Such structures can provide better liquid absorption performance whilst retaining good product integrity, both in a dry and wet state.

Figure 17:
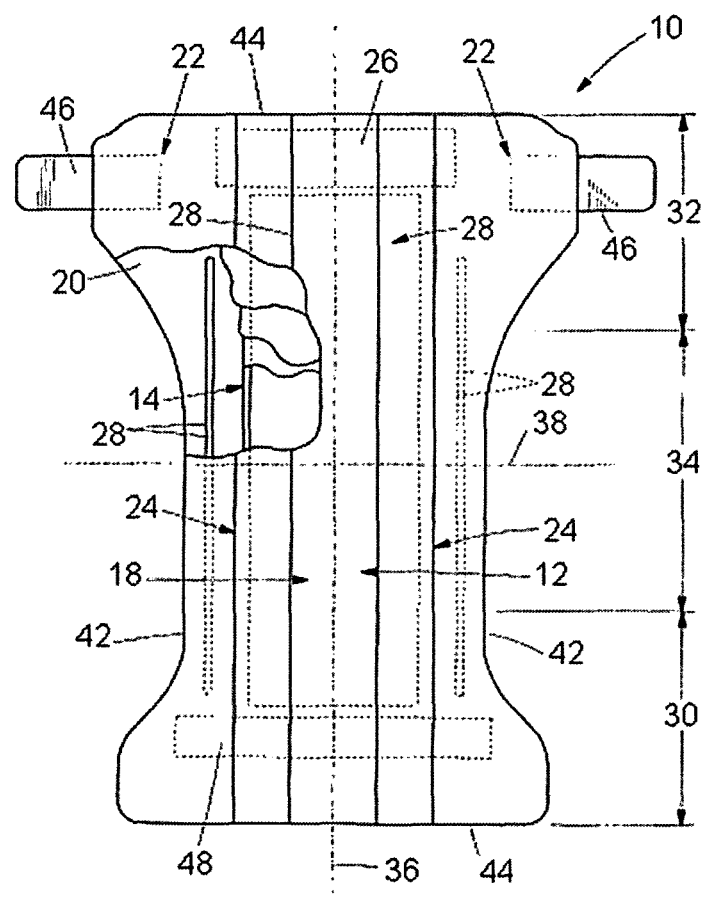
FIG. 17 is a top plan view of a diaper as a preferred embodiment of an absorbent article according to the invention, with the upper layers partially cut away.

FIG. 17 is a top plan view of a diaper 10 as a preferred embodiment of an absorbent article including an absorbent structure according to the present invention. It should be understood, however, that the present invention is also applicable to other absorbent articles such as feminine hygiene garments, baby pants, adult incontinent garments and the like.

The absorbent article is shown in its flat out, un-contracted state with the wearer side facing the viewer. Portions of the absorbent article are cut away to more clearly show the underlying structure of the diaper 10 including the absorbent elements and absorbent components. The chassis 12 of the diaper 10 in FIG. 17 comprises the main body of the diaper 10. The chassis 12 comprises an outer covering including a liquid pervious top sheet 18 and/or a liquid impervious back sheet 20. The chassis 12 may include a portion of an absorbent structure 14 encased between the top sheet 18 and the back sheet 20. The chassis 12 may also include most or all of the absorbent structure 14 encased between the top sheet 18 and the back sheet 20. The chassis 12 preferably further includes side panels or ears 22, elasticized leg cuffs 24 and elastic waist features 26, the leg cuffs 24 and the elastic waist feature 26 each typically comprise elastic members 28. One end portion of the diaper 10 is configured as a front waist region 30 of the diaper 10. The opposite end portion is configured as a back waist region 32 of the diaper 10. An intermediate portion of the diaper 10 is configured as a crotch region 34, which extends longitudinally between the first and second waist regions 30 and 32. The waist regions 30 and 32 may include elastic elements such that they gather about the waist of the wearer to provide improved fit and containment (e.g. elastic waist feature 26). The crotch region 34 is that portion of the diaper 10 which, when the diaper 10 is worn, is generally positioned between the wearer's legs. The diaper 10 is depicted with its longitudinal axis 36 and its transverse axis 38. The periphery of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper. The chassis 12 also comprises a fastening system, which may include at least one fastening or securing member 46 and at least one landing zone 48. The various components within the diaper 10 may be bound, joined or secured by any method know in the art, for example by adhesives in uniform continuous layers, patterned layers or arrays of separate lines, spirals or spots. The top sheet 18, the back sheet 20, the absorbent structure 14 and other components may be assembled in a variety of well-known configurations and are well known in the art.

The back sheet 20 covers the absorbent structure 14 and preferably extends beyond the absorbent structure 14 toward the longitudinal edges 42 and end edges 44 of the diaper 10 and may be joined with the top sheet 18. The back sheet 20 prevents the bodily exudates absorbed by the absorbent structure 14 and contained within the diaper 10 from soiling other external articles that may contact the wearer, such as bed sheets and undergarments. In preferred embodiments, the back sheet 20 is substantially impervious to bodily exudates and comprises a laminate of a nonwoven and a thin plastic film such as a thermoplastic film. The back sheet 20 may comprise breathable materials that permit vapour to escape from the diaper 10 while still preventing bodily exudates from passing through the back sheet 20. It may be semi-rigid, non-elastic and can be made fully or partially elasticized and include backing. The back sheets 20 may be assembled in a variety of well-known configurations and are well known in the art.

The diaper 10 comprises a top sheet 18 that is preferably soft, compliant, exhibits good strikethroughs and has a reduced tendency to rewet from the liquid absorbent material. The top sheet 18 is placed in close proximity to the skin of the wearer when the diaper 10 is worn. In this way, such top sheet 18 permits bodily exudates to rapidly penetrate it so as to flow toward the absorbent structure 14 more quickly, but preferably not allowing such bodily exudates to flow back through the top sheet 18. The top sheet 18 may be constructed from any one of a wide range of liquid and vapour permeable, preferably hydrophilic, materials. The upper and lower surface of the top sheet 18 may be treated differently and may for instance include a surfactant on the upper surface so as to facilitate liquid transfer there through, especially at a central zone or area of the top sheet 18 located over the absorbent structure 10, and for instance include a hydrophobic agent on the lower surface to minimize the liquid contained within the absorbent core from contact wetting the top sheet 18 thereby reducing rewet values. The top sheet 18 may also be coated with a substance having rash preventing or rash reducing properties (e.g. aloe vera). The top sheet 18 covers substantially the entire wearer facing area of the diaper 10, including substantially all of the front waist region 30, back waist region 32, and crotch region 34. Further, the side panels 22 and/or waist feature layers of the inner region may be formed from the same single top sheet material and, thus, may be referred to as being unitary with the top sheet 18 in forming longitudinal and lateral extensions of the top sheet 18 material. Alternatively, the top sheet 18 may be formed from multiple different materials which vary across the width of the top sheet 18. Such a multiple piece design allows for creation of preferred properties and different zones of the top sheet 18. The top sheet 18 be semi-rigid, non-elastic and can be made fully or partially elasticized. The top sheet 18 may be assembled in a variety of well-known configurations and are well known in the art.

The absorbent structure 14 in FIG. 17 generally is disposed between the top sheet 18 and the back sheet 20. The absorbent structure 14 may comprise any absorbent material 110 that is generally compressible, conformable, non-irritating to the wearer's skin, and capable of absorbing and retaining bodily exudates. The absorbent structure 14 may comprise a wide variety of liquid absorbent materials 110 commonly used in absorbent articles such as fluff pulp, which is generally referred to as airlaid. Examples of other suitable absorbent materials include creped cellulose wadding; melt blown polymers; chemically stiffened, modified or cross-linked cellulosic fibres; tissue, including tissue wraps and tissue laminates; absorbent foams; absorbent sponges; absorbent polymer materials; absorbent gelling materials; or any other known absorbent materials or combinations of materials. The absorbent structure 14 may further comprise minor amounts (typically less than 10%) of non-liquid absorbent materials, such as adhesives, binders, plastics, waxes, oils and the like. The absorbent structure 14 according to various embodiments of the invention may be configured to extend substantially the full length and/or width of the diaper 10. However, alternatively the absorbent structure 14 according to the invention is not coextensive with the entire diaper 10 and is limited to certain regions of the diaper 10 such as for instance the crotch region 34. In various embodiments, the absorbent structure 14 extends to the edges of the diaper 10 and the absorbent material 110 is concentrated in the crotch region 34 or another target zone of the diaper 10. In still another embodiment, the particles can be a combination of absorbent material 110, preferably comprising absorbent polymer material, and skin care particles such as ion exchange resins, deodorant, antimicrobial agents, binder particles, or other beneficial particles.

The diaper 10 may also utilize a pair of containment walls or cuffs 24. Each cuff 24 is a longitudinally extending wall structure preferably positioned on each side of the absorbent structure 14 and spaced laterally from the longitudinal axis 36. The longitudinal ends of the cuffs 24 may be attached or joined, for example, to the top sheet 18 in the front and rear waist regions 30 and 32. Preferably, the ends of the cuffs 24 are tacked down inwardly and attached, for example, by adhesive or sonic bonding to the lower structure. Such a construction effectively biases the cuffs 24 inwardly and is generally considered to cause the cuffs 24 to exhibit improved leakage prevention properties. Preferably, the cuffs 24 are equipped with elastic members 28, which extend along a substantial length of the cuffs 24. In a common application, the elastic members 28 are placed within the cuffs 24, preferably at the top of the cuff 24 while in a stretched condition and then glued or sonic bonded to the cuff 24 at least at their ends. When released or otherwise allowed relaxing, the elastic members 28 retract inwardly. When the diaper 10 is worn, the elastic members 28 function to contract the cuffs 24 about the buttocks and the thighs of the wearer in a manner, which forms a seals between the diaper 10, the buttocks and the thighs. The cuffs 24 may be assembled in a variety of well-known configurations and are well known in the art.

The diaper 10 may also employ additional layers known in the art including an acquisition layer or surge layer, preferably situated between the top sheet and the absorbent core and highloft and/or coverstock layers. This serves to slow down the flow so that the liquid has adequate time to be absorbed by the absorbent core.

In order to keep the diaper 10 in place about the wearer, preferably at least a portion of the back waist region 32 is attached by fastening or securing members 46 to at least a portion of the front waist region 30, preferably to form leg openings and an absorbent article waist. Fastening or securing members 46 carry the tensile load around the absorbent article waist and compliment the elastic members 28 by providing a quasi-seal between the wearer, the elastic waist feature 26 and cuffs 24, so that bodily exudates are contained within the diaper 10 which are then absorbed. In other words, so that it does not leak through gaps between the wearer and the edge of the diaper 10. The fastening or securing members 46 may for instance be adhesive, mechanical fasteners, hook and loop features, conceivable strings and/or combinations thereof, i.e., anything that will secure one end of the diaper 10 to the longitudinally opposite end of the diaper 10. The fastening or securing members 46 may also be co-adhesive such that they adhere to each other but not other materials. The fastening or securing members 46 and any component thereof may include any material suitable for such a use, including but not limited to plastics, films, foams, non-woven webs, woven webs, paper, laminates, fibre reinforced plastics and the like, or combinations thereof. It may be preferable that the materials making up the fastening or securing members 46 are flexible, extensible and/or elastic, allowing them to better conform to the shape and movements of the body and thus, reduces the likelihood that the fastening system will irritate or injure the wearer's skin. Preferably, the diaper 10 is affixed to the wearer by tape fasteners which are permanently affixed to the back sheet 20. Tape fasteners are contacted with the transversely opposite side panel or ears 22 attached or joined and extending from the back sheet 20, where they remain affixed due to the binding compound applied to the fasteners. Alternatively, the absorbent article may be pants and the like. In this configuration, the absorbent article may or may not have tape fasteners. Specific disposability tapes may however also be provided on such absorbent articles. All fastening and securing elements 46 may be assembled in a variety of well-known configurations and are well known in the art.

The waist regions 30 and 32 each comprise a central region and a pair of side panels or ears 22 which typically comprise the outer lateral portions of the waist regions. These side panels 22 may be unitary with the chassis 12 and/or back sheet 20 or may be attached or joined thereto by any means know in the art. In a preferred embodiment of the present invention, the side panels 22 positioned in the back waist region 32 are flexible, extensible and/or elastic in at least the lateral direction (i.e., elasticized side panels), in another embodiment the side panels 22 are non-elastic, semi-rigid, rigid and/or stiff. These variety of side panels 22 are well known in the art.

Furthermore waistbands 26 employing elastic members can be positioned along the transverse portion of the diaper 10 so that when worn, the waistbands 26 are positioned along the waist of the wearer. Generally, the waistband 26 preferably creates a seal against the waist so that bodily exudates do not leak from the regions between the elastic waistband 26 and the waist of the wearer. Although the bodily exudates are primarily absorbed by the absorbent materials within the diaper 10, the seal is important considering the assault of liquid by the wearer may overwhelm the absorption rate capacity of the absorbent structure 14. Hence, the waistbands 26 contain the liquid while it is being absorbed, they are well known in the art.

The absorbent article such as a diaper 10 may also include such other features, components and elements as are known in the art including front and rear ear panels, waist cap features, elastics and the like to provide better fit, containment and aesthetic characteristics. These features may be assembled in a variety of well-known configurations and are well known in the art.

The process for producing preferred absorbent structures in accordance with the present invention comprises the following steps: A carrier layer 101 is provided onto which absorbent material 110 is disposed by methods known in the art. To deposit the absorbent material 110, vacuum, gravity or other forces can be used. Then an auxiliary layer 102 is provided, covering the absorbent material 110, and primary bonding regions 111 and secondary bonding regions 115 are being provided. In case one would like to use adhesives or chemical binders, then it might be useful to attach these to the carrier layer 101 and/or auxiliary layer 102 layer prior to bringing the sandwich structure together. In case one opts for thermo-sealed bonding areas, then the thermo-sealing can be applied after the sandwich structure components have been brought together. It is of course also possible to combine both techniques in the same absorbent structure.

The invention claimed is:

1. A substantially cellulose free absorbent structure for use in an absorbent article comprising a carrier layer and an auxiliary layer and an absorbent material provided there between, and attachments for intermittently joining said carrier layer and auxiliary layer together, said attachments being made up of substantially permanent primary attachment grids and substantially temporary secondary attachment patterns with secondary bonding regions which correspond with the secondary attachment pattern, so as to form a sandwich-like composite structure containing patterned absorbent particulate polymer materials provided in at least some of the unattached regions between the carrier layer and auxiliary layer forming defining an absorbent polymer material area, joining said carrier layer and said auxiliary layer at least partially together and thereby immobilising dry absorbent polymer material in a plurality of substantially temporary smaller-sized pockets comprising at least some of the substantially temporary secondary attachments wherein under the influence of liquid the absorbent composite structure is loosened at the substantially temporary secondary attachments to form substantially permanent bigger-sized compartments comprising substantially permanent primary attachments thereby immobilising the volume-expanded wetted absorbent polymer materials, wherein said attachments are at least partially formed via a thermal, mechanical, thermo-mechanical, chemical and/or ultrasonic process, wherein the secondary bonding regions consist of various sub-regions, corresponding with different separation forces, whereby the secondary bonding regions consist of weaker secondary bonding regions and stronger secondary bonding regions where weaker secondary bonding regions loosen faster than the stronger secondary bonding regions.

2. The absorbent structure according to claim 1 wherein the substantially permanent primary attachment grids after detachment of at least part of the substantially temporary secondary attachment patterns provide an internal fluid management.

3. The absorbent structure according to claim 1, wherein the substantially permanent primary attachment grids after detachment of at least part of the substantially temporary secondary attachment patterns swells non-homogeneously and/or phased to form a superficial liquid management structure.

4. The absorbent structure according to claim 1, wherein the substantially permanent primary attachment grid and/or substantially temporary secondary attachment pattern is distributed over substantially the majority of the surface area of the absorbent polymer material area.

5. The absorbent structure according to claim 1, wherein at least some or all of the substantially permanent primary attachments and/or substantially temporary secondary attachments are formed with at least an adhesive or binder as attachment medium and/or immobilization layer.

6. The absorbent structure according to claim 1, wherein the substantially permanent primary attachments and/or substantially temporary secondary attachments have different locations, sizes and/or shapes.

7. The absorbent structure according to claim 1, wherein the bond strength of at least some of the substantially permanent primary attachments is higher than the bond strength of at least some of the substantially temporary secondary attachment in dry and/or wet state.

8. The absorbent structure according to claim 1, where the distance in between some of the substantially permanent primary attachments are at least 2 mm apart from each other.

9. The absorbent structure according to claim 1, where the distance in between some of the substantially temporary secondary attachments are at least 2 mm apart from each other.

10. The absorbent structure according to claim 1, wherein at least 80% of the absorbent material is absorbent polymer material.

11. The absorbent structure according to claim 1, wherein the absorbent structure has on average within the absorbent polymer material area at least one pocket per about 45 $cm^2$.

12. The absorbent structure according to claim 1, wherein at least some or all of the substantially permanent primary attachments and/or substantially temporary secondary attachments have an average surface size of at least 0.3 $mm^2$.

13. The absorbent structure according to claim 1, wherein at least a paper, non-woven, thermoplastic layer and/or immobilization layer is provided.

14. The absorbent article comprising an absorbent structure according to claim 1, wherein said absorbent article is a feminine hygiene garment, baby diaper, baby pants or adult incontinence garment.

15. The absorbent article comprising a liquid pervious topsheet, a liquid impervious backsheet and a liquid absorbing absorbent structure situated in between the liquid pervious topsheet and liquid impervious backsheet according to claim 1.

16. The method for the manufacturing of an absorbent structure according to claim 1 which comprises: providing a carrier layer, covering the carrier layer with an absorbent material, covering the absorbent material with an auxiliary layer which is joinable to the carrier layer; and in at least one position substantially temporary and substantially permanently attaching the auxiliary layer to the carrier layer, and by means of at least substantially temporary secondary attachments defining small-sized pocket wherein dry absorbent material is immobilized, such that by means of gradual release of substantially temporary secondary attachment patterns bigger-sized compartments are provided, thereby continuously immobilising the absorbent material from dry to wet state.

17. The absorbent structure according to claim 1 wherein the absorbent structure consists of weaker secondary bonding regions at a periphery of the absorbent structure.

* * * * *